United States Patent [19]

Sakamoto et al.

[11] Patent Number: 5,023,089
[45] Date of Patent: Jun. 11, 1991

[54] SUSTAINED-RELEASE PREPARATIONS AND THE PROCESS THEREOF

[75] Inventors: Teruo Sakamoto, Osaka; Toyohiko Takeda, Hyogo; Yusuke Suzuki, Osaka, all of Japan

[73] Assignee: Shionogi & Co., Ltd., Osaka, Japan

[21] Appl. No.: 379,631

[22] Filed: Jul. 13, 1989

[30] Foreign Application Priority Data

Jul. 18, 1988 [JP] Japan .................... 63-178757

[51] Int. Cl.$^5$ .............................. A61K 9/50
[52] U.S. Cl. ........................ 424/502; 424/498; 424/489
[58] Field of Search ............ 424/502, 498, 489

[56] References Cited

U.S. PATENT DOCUMENTS 2,805,977  9/1957  Robinson ..................... 167/82
3,487,138 12/1969  Hess .......................... 264/112
4,865,851  9/1989  James ......................... 424/498

FOREIGN PATENT DOCUMENTS 0043254  1/1982  European Pat. Off. .
0254978  2/1988  European Pat. Off. .
63-24978  5/1988  Japan .
WO89/02742  4/1989  PCT Int'l Appl. .

OTHER PUBLICATIONS

Kumar et al., Chem. Abst., vol. 84, No. 12, 22 Mar. 1976, p. 385, Abstact No. 79641a.
Socias et al., Chem. Abst., vol. 92, No. 6, 11 Feb. 1980, p. 331, Abstract No. 47182a.
Ahmed et al., Chem. Abst., vol. 95, No. 1, 13 Jul. 1981, p. 359, Abstract No. 12671u.

Primary Examiner—Thurman K. Page
Assistant Examiner—D. Gabrielle Phelan
Attorney, Agent, or Firm—Wenderoth, Lind & Ponack

[57] ABSTRACT

Sustained-release preparations essentially consisting of 1 part by weight of a water-soluble active ingredient and 1 to 10 parts by weight of two or more fats where the melting point is different in one from others, being capable of releasing active ingredients at a constant rate for a long-period of time, and being manufactured easily and economically.

3 Claims, 2 Drawing Sheets

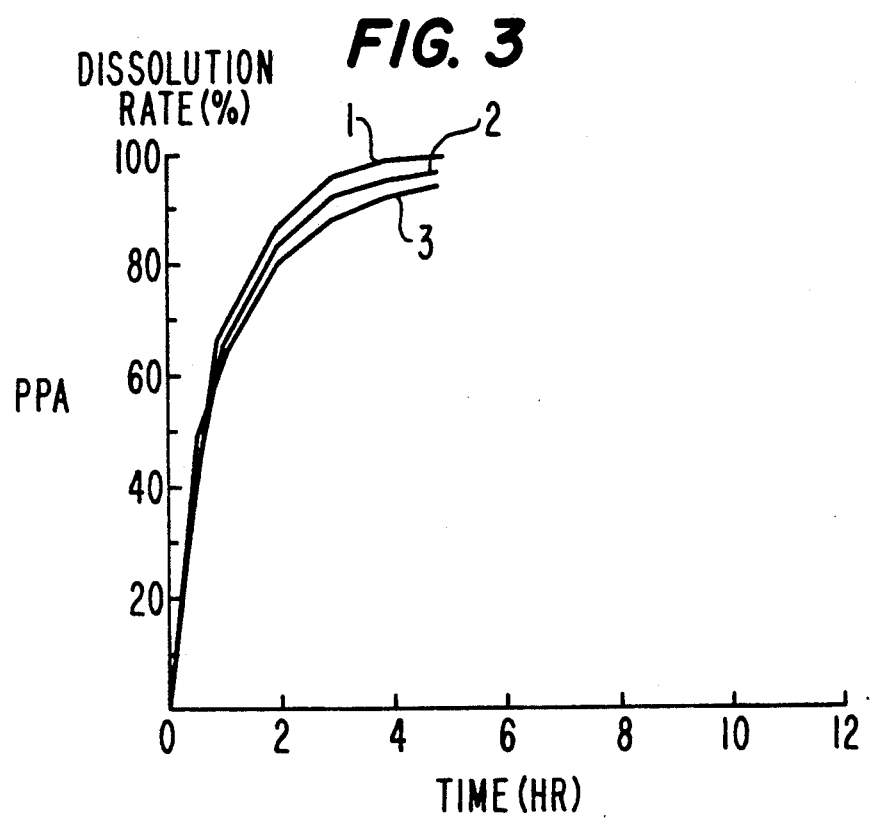

5,023,089

SUSTAINED-RELEASE PREPARATIONS AND THE PROCESS THEREOF

BACKGROUND OF THE INVENTION

1. Field of Invention

This invention relates to long-acting preparations which have actions of both rapid-release and sustained-release in spite of their single unit dosage form, and also to the process of manufacturing said preparations. In the manufacturing process of this invention, neither organic solvents nor water are used. Therefore, there is no danger of explosion. Nor is there any problem of residual solvent. Also it does not require a drying process. Thus, this process makes it possible to manufacture said sustained-release preparations easily and at a low cost.

2. Prior Art

Some methods have been reported concerning the technique of making sustained-release by effectively controlling the dissolution of water-soluble active ingredient with the use of melted fats. Such technique is divided into two main types: one is a method of making sustained-release by forming a matrix or by making a solid dispersion and the other is that of making a membrane, reservoir type preparation by coating the fats.

The method disclosed in KOKOKU No. 63-24978 belongs to the latter and attains sustained-release extending over a period of 8 hours or longer by coating an emulsion of fats in water onto the active ingredient. However, this method has a drawback in that since a W/O type emulsion of fat is spray-coated on the granules prepared beforehand, (a) it involves processes of making granules and of drying the granules, (b) it also involves further processes of drying after spray coating, etc., and (c) it requires the use of a surfactant in making an emulsion, by which a problem in safety is caused.

SUMMARY OF INVENTION

The present invention provides sustained-release preparations essentially consisting of 1 part by weight of a water-soluble active ingredient and 1 to 10 parts by weight of two or more fats where the melting point is different in one from others and also provides unique processes for manufacturing said novel sustained-release preparations, characterized in that 1 part by weight of a water-soluble active ingredient is suspended or melted in 1 to 10 parts by weight of a mixed melt consisting of two or more fats having different melting points, and while the temperature of the suspension or melt is maintained at a level higher than the solidification point of the fat having a higher melting point, said suspension or melt is formulated into granules by means of spray-cooling, and then the granules obtained are annealed at a temperature (hereafter this temperature is mentioned as "annealing temperature") which is lower than the melting point of the fat having a higher melting point but is higher than the melting point of the fat having a lower melting point.

The thus prepared preparations attain zero-order release of the drug for a long period of time.

BRIEF DESCRIPTION OF DRAWINGS

FIG. 3 shows the relationship between the amount of the active ingredient released from each reference preparation versus the lapse of time. The ordinate shows the dissolution rate (%) of PPA and the abscissa shows the time. The curves indicated by 1-3 are the dissolution curves on preparations of Reference Examples 1 to 3 in the second fluid, respectively.

DESCRIPTION OF PREFERRED EMBODIMENT

Problems to be Solved

Figure 1:
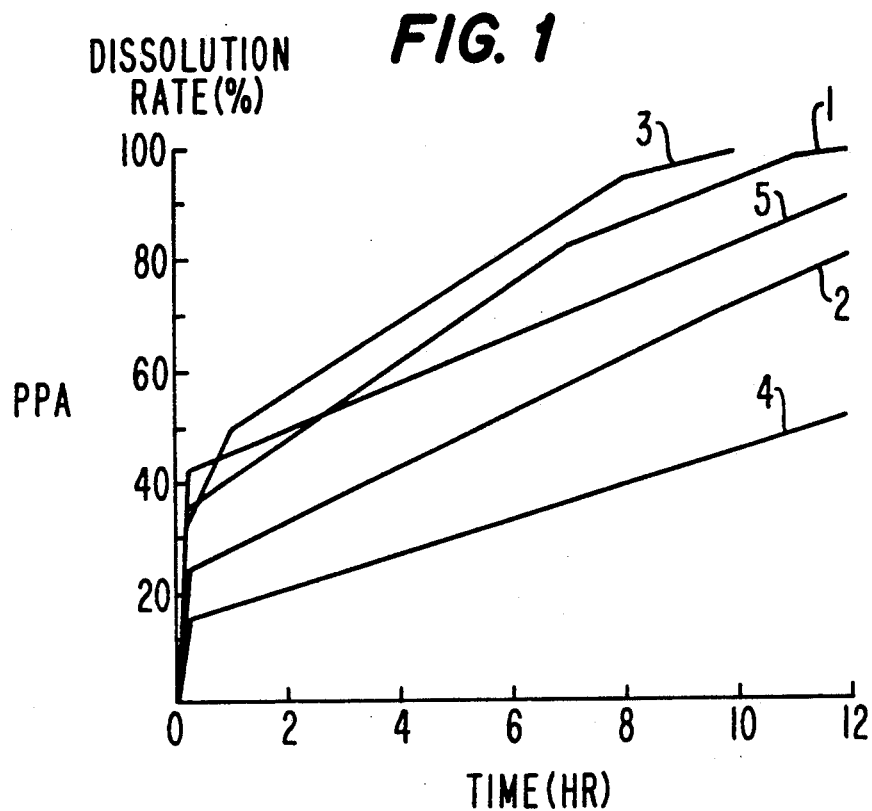
FIG. 1 shows the relationship between the amount of the active ingredient released from each preparation of this invention versus the lapse of time. The ordinate shows the dissolution rate (%) of PPA and the abscissa shows the time. The curves indicated by 1-5 are the dissolution curves on preparations of Examples 1 to 5 in the second fluid (Pharmacopoeia of Japan, 11th Edition), respectively.

As mentioned above, when sustained-release preparations are made with the use of a melt of fats, it is impossible by a simple spray-coating method to obtain sophisticated zero-order controlled release of pharmaceutical substance. Therefore, special contrivances are used in coating, etc. as disclosed in KOKOKU 63-24978. However, such processes are complicated, and take a long time to be done, which are the drawbacks of this method. In making conventional long-acting preparations, rapid-release preparations which are independently prepared have been admixed with sustained-release preparations, or a rapid releasing portion has been coated on sustained-release preparations, and so forth. However, such operations are troublesome. This is a weak point of the conventional method.

Means to Solve the Problems

In view of the above circumstances, the inventors tried to develop a simple method by which zero-order sustained-release preparations could be made (especially, without a drying process), and have perfected this invention, after strenuous studies. This invention relates to zero-order sustained-release preparations and to the process thereof. This invention provides simple and economical but unique methods of manufacturing zero-order sustained-release preparations capable of releasing active ingredient at a constant rate over a period of 10 hours or longer. In this manufacturing method, a melt or suspension of fats containing a water-soluble active ingredient is made into granules by a simple spray cooling and then the granules obtained are annealed.

A study of dissolution patterns on the sustained-release preparations manufactured by the method of this invention shows that there are two phases on drug releasing. One is located at an earlier stage where an active ingredient is first released rapidly, and the other is at the later stage where an active ingredient is released gradually. That is to say, 20-30% of the active ingredient is released rapidly within 10 minutes, and the remainder is released at a zero-order over a long period of time. According to the method of this invention, preparations which give rapid and long-acting pharmacological effects can be readily manufactured at a low cost, without special process of making a rapid releasing part.

This invention is especially useful for the preparation of such active ingredients as are absorbed rapidly through an extensive area of the digestive tract but have short action. This invention does not exclude the coating, on the present sustained-release preparation, an additional active ingredient as a rapid-release portion or the different kind of active ingredients which should be released rapidly. By so doing, a wider range of preparations can be designed, thus making it possible to easily manufacture preparations with a desired pattern of release.

As for fats to be used in this invention, any fat can be used as long as it is pharmacologically inert and has no interaction with any of the water-soluble pharmaceutical active ingredients used. Representatives of such fats are exemplified below, showing their melting points in parentheses. It should be noted, however, that some of them are sold in various grades and melting points generally vary with the grade. Therefore, they should be used after confirming their melting points.

Hydrogenated castor oil (79°–88° C.), hydrogenated beef tallow (oil) (38°–62° C.), hydrogenated lard oil (38°–62° C.), cacao butter (45°–50° C.); fatty acid glycerol esters such as glycerol monolaurate (44°–63° C.), glycerol monomyristate (56°–70.5° C.), glycerol monopalmitate (66.5°–77° C.), glycerol monostearate (74.5° C.), glycerol dilaurate (39°–54° C.), glycerol dimyristate (54°–63° C.), glycerol dipalmitate (50°–72.5° C.), glycerol distearate (71°–77° C.), glycerol trimyristate (44°–55.5° C.), glycerol tripalmitate (55.5°–65.5° C.), glycerol tristearate (64°–73.1° C.); wax material such as beeswax (60°–67° C.), carnauba wax (80°–86° C.), Japan wax (50°–54° C.), and spermaceti (42°–54° C.); hydrocarbons such as paraffin (50°–75° C.), microcrystalline wax (74°–91° C.); fatty alcohols such as cetyl alcohol (47°–53° C.), stearyl alcohol (56°–62° C.); and higher fatty acids such as lauric acid (42°–42.2° C.), myristic acid (53.4°–53.6° C.), palmitic acid (63.8°–64.0° C.), stearic acid (70.7° C.), behenic acid (86°–86.3° C.), and arachic acid (77.5°–77.7° C.).

In the method of this invention, since two or more fats are used as a mixture, one having a higher melting point than the other is called fat having a higher melting point, and the other is called fat having a lower melting point. Therefore, in this invention, the term "higher melting point" or "lower melting point" does not mean the absolute values, but indicates a relative one in comparison between two or more fats selected. It is preferable that a fat having a melting point of 60° C. or higher is used as the one having higher melting point, and at the same time, it is preferable that there is a difference of at least 10° C. between the melting points of the two fats to be used.

The sustained-release preparations of this invention are manufactured as follows: First, two fats having different melting points from each other are selected, both of which are insoluble or sparingly soluble in water. Next, 1 part by weight of the fat having a higher melting point is mixed with 0.05–1.0 part by weight, preferably 0.2–0.5 part by weight, of the fat having a lower melting point, and the mixture is heated at 90°–120° C. to give a melt. When the addition ratio of the fat having a lower melting point is higher than the upper limit mentioned above, it becomes difficult to maintain the original form of the granules through the manufacturing processes, and when the ratio is lower than the lower limit, it becomes impossible to obtain zero-order sustained-release preparations. Powdery active ingredient is added to the aforementioned melt at a rate of 10–100%, preferably 25–100% by weight to the total weight of the fats employed, while the melt is kept at 100°–120° C. The thus obtained suspension or melt is then subjected to spray cooling under the conditions at a spraying temperature of 110° C. and at a cooling temperature of 20°–40° C., whereby homogenized granules or beads are obtained. By annealing said granules or beads in a drier or the like at the annealing temperature for 30 minutes to 2 hours, sustained-release preparations can be obtained.

Under a microscopic observation, it can be seen that the granules before being annealed have a rough surface which is pierced deeply with many holes, however, the surface of the granules after being annealed is very smooth. It can be considered that this is because only the fat having a lower melting point located at the surface of the granule is melted and flows into the holes in the annealing process, thereby a certain amount of the active ingredient located in the outer parts of the granules comes out. Incidentally, the surface of the granule becomes very smooth even microscopically. That is to say, the granules of this invention each is structured, from the outside, by (a) a smooth layer where fine solids of the active ingredient and of the two different kinds of fats are very closely gathered and (b) a matrix core which is rather roughly structured by the active ingredient and the fats.

From this structure, it is presumed that the active ingredient is released from the preparations by the following mechanism:

When a preparation reaches the stomach, the gastric juice dissolves the exposed active ingredient, and the dissolved ingredient is released rapidly. Then, the juice permeates into the matrix core through the smooth layer and dissolves the ingredient gradually. The dissolved active ingredient is dispersed in the rough core and then released out gradually through the smooth layer. At this stage, the concentration of the active ingredient in the rough core is kept in a steady state, whereby, as a result, a zero-order releasing pattern is attained over a long period of time. It is to be noted here that the above presumption on the mechanism is not intended to limit the scope of this invention.

As regards active ingredients to be used in this invention, any active ingredient can be used as long as it is soluble in water, and it is preferable if the active ingredient is such as can be absorbed through an extensive area of the digestive tract. The term "water-soluble active ingredient" as used in this invention includes not only pharmaceutical substances ordinarily soluble in water but also those which are sparingly water-soluble at or around the neutral point, but are soluble in acidic or alkaline aqueous medium (in the stomach or the intestines).

Representatives of such pharmaceutical substances are exemplified below, but these do not limit the scope this invention in any way:

Antihistamines such as chlorpheniramine maleate, d-chlorpheniramine maleate (hereafter abbreviated as d-CPM), clemastine fumarate, carbinoxamine maleate, promethazine hydrochloride, and diphenhydramine salicylate (hydrochloride); analgesics and antipyretics such as aspirin, salicylamide, ethenzamide, acetaminophen, and diclofenac sodium; antitussives and expectorants such as dextromethorphan hydrobromide, dihydrocodeine phosphate, cloperastine hydrochloride, phenylpropanolamine hydrochloride (hereafter abbreviated as PPA), methylephedrine hydrochloride, potassium cresol sulfonate, potassium guaiacol sulfonate, and belladonna total alkaloids; drugs for gastric ulcers such as pirenzepine hydrochloride, cetraxate, ranitidine, and famotidine; drugs for circulatory organs such as pindolol, propranolol hydrochloride, alprenolol hydrochloride, oxprenolol hydrochloride, diltiazem hydrocloride, and pinacidil; antitumor drugs such as cisplatin, 5-fluorouracil, and tegafur; and synthetic antibacterial agents such as cinoxacin and enoxacin.

Since the sustained-release preparations of this invention are not dependent on pH, they are expected to exhibit the same releasing properties in aged patients or patients with gastric subacidity or anacidity as in healthy adults.

This invention is explained in more detail by the following Examples or Experiments, which are not intended to limit the scope of this invention.

EXAMPLES

General Procedures

Granulation Process

A fat of a higher melting point (hereafter mentioned as fat A) and a fat of a lower melting point (hereafter mentioned as fat B) are placed in a 1 L stainless mug and heated up to 90°–120° C. (melting temperature) with a mantle heater to give a melt. An active ingredient with a size through 80 mesh is suspended or melted in the melt, during the time of which the melt is kept at a temperature of 100°–120° C. under stirring (500 r.p.m.) with a screw-type stirrer. The suspension or melt thus obtained is manufactured into beads of 300–500 μmϕ in diameter, using an atomizing type spray cooling apparatus equipped with a single fluid nozzle at a spraying temperature of 110° C. and a cooling temperature of 20°–40° C.

Annealing Process

The thus obtained beads are treated in a drier at the annealing temperature for 30 minutes to 2 hours (treating time) and then cooled to room temperature to give a sustained-release preparation.

EXAMPLES 1-7

Sustained-release preparations shown in Table 1 were manufactured by the afore-mentioned General Procedures.

In these Examples or Reference Examples, the following substances were used:

As hydrogenated castor oil, Lovely Wax® 101 (melting point 79°–88° C.: Freund Sangyo); as hydrogenated beef oil, Triphate® −52 (melting point 49°–54° C.: Nikko Chemical); as carnauba wax, Polishing Wax® 103 (melting point 80°–86° C.: Freund Sangyo); as beeswax, Bleached Beeswax (melting point 60°–67° C.: Miki Chemical); and as glycerol dipalmitate, a material of special reagent grade (melting point 50°–55° C.: Bansei Chemical).

REFERRENCE EXAMPLE 1-3

In substantially the same manner as in General Procedures, reference compositions shown in Table 1 were manufactured.

TABLE 1

|  | THIS INVENTION | | | | |
| --- | --- | --- | --- | --- | --- |
|  | Example 1 | Example 2 | Example 3 | Example 4 | Example 5 |
| Active Ingredient | PPA: 200 g | PPA: 200 g | PPA: 200 g | PPA: 200 g | PPA: 200 g |
| Fat A | Hydrogenated castor oil: 240 g | Hydrogenated cator oil: 320 g | Carnauba wax: 250 g | Stearic acid: 80 g | Carnauba wax: 250 g |
| Fat B | Hydrogenated beef oil: 60 g | Hydrogenated beef oil: 80 g | Bees wax: 62 g | Glycerol dipalmitate: 80 g | Bees wax: 120 g |
| Temp. for Melting | 100° C. | 100° C. | 100° C. | 100° C. | 100° C. |
| Spraying Temp. | 110° C. | 110° C. | 110° C. | 110° C. | 110° C. |
| Cooling Temp. | 30° C. | 30° C. | 25° C. | 20° C. | 25° C. |
| Annealing Temp. | 65° C. | 65° C. | 70° C. | 45° C. | 70° C. |
| Treating Time | 2 Hours | 2 Hours | 1 Hour | 0.5 Hours | 1 Hour |
| Mean Particle Size | 450 μmϕ | 450 μmϕ | 450 μmϕ | 450 μmϕ | 500 μmϕ |
| Granules Obtained | 440 g | 546 g | 473 g | 607 g | 512 g |
|  | THIS INVENTION | | Control (PRIOR ART) | | |
|  | Example 6 | Example 7 | Reference 1 | Reference 2 | Reference 3 |
| Active Ingredient | d-CPM: 100 g | Vitamin B₁ mononitrate: 100 g | PPA: 200 g | PPA: 200 g | PPA: 200 g |
| Fat A | Hydrogenated castor oil: 320 g | Carnauba wax: 210 g | Hydrogenated castor oil: 400 g | Hydrogenated castor oil: 400 g | Hydrogenated castor oil: 240 g |
| Fat B | Hydrogenated beef oil: 80 g | Cetyl Alcohol: 140 g | — | — | Hydrogenated beef oil: 60 g |
| Temp. for Melting | 100° C. | 100° C. | 100° C. | 100° C. | 100° C. |
| Spraying Temp. | 110° C. | 110° C. | 110° C. | 110° C. | 110° C. |
| Cooling Temp. | 30° C. | 30° C. | 30° C. | 30° C. | 30° C. |
| Annealing Temp. | 65° C. | 60° C. | — | — | — |
| Treating Time | 1 Hour | 1 Hour | — | — | — |
| Mean Particle Size | 450 μmϕ | 450 μmϕ | 450 μmϕ | 450 μmϕ | 450 μmϕ |
| Granules Obtained | 430 g | 400 g | 550 g | 550 g | 420 g |

EXAMPLE 8

Manufacturing of long-acting preparations 500 grams of the sustained-release beads prepared in Example 2 is powder-coated, by using a super mixer, a mixture of d-CPM (5 g), hydrogenated castor oil (10 g), and lactose (22 g) each of which was passed through 80 mesh screen, during the time of which 65 g of 2% aqueous solution of methylcellulose as a binder is sprayed to the same at a rate of 12 g per minute. The thus obtained preparations are dried and dressed under aeration at 55° C. for an hour to give twice-layered beads having a mean particle size of 500 μmϕ. The thus obtained beads are distributed into capsules (No. 4) by 451 mg each to give the objective long-acting preparation. Each capsule preparation contains 70 mg of PPA and 4 mg of d-CPM.

EXPERIMENT 1

The preparations obtained in Examples 1–5 were subjected to dissolution test (paddle method), using the second fluid according to the Pharmacopoeia of Japan, 11th Edition. In each test, such an amount of beads as to contain 50 mg of PPA was used. Every preparation released rapidly 15 to 45% of the active ingredient in 10 minutes, and then the remainder was released gradually in a practically zero-order release. The results are shown in FIG. 1.

EXPERIMENT 2

Figure 2:
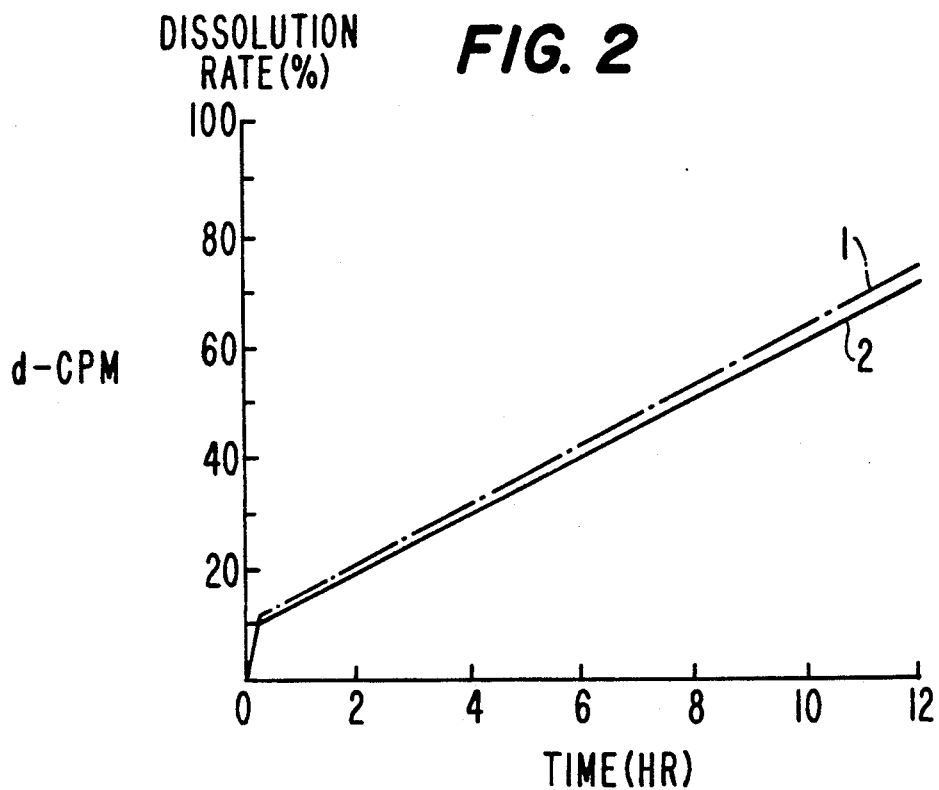
FIG. 2 shows the relationship between the amount of the active ingredient release from the preparation of this invention versus the lapse of time. The ordinate shows the dissolution rate (%) of d-CPM and the abscissa shows the time. The curve indicated by 1 is the dissolution curve on the preparation of Example 6 in the first fluid and the curve 2 is that in the second fluid.

Dissolution test (paddle method) in the first and the second fluids was carried out on the preparation obtained in Example 6, according to the Pharmacopoeia of Japan, 11th Edition. In each test, such an amount of beads as to contain 5 mg of d-CPM therein was used. In both tests, the preparation released rapidly 10% of the active ingredient within 10 minutes and then the remainder in a pattern close to zero-order. From the above, it was confirmed that the preparations of this invention are independent of pH conditions. The results are shown in FIG. 2.

EXPERIMENTAL 3

Dissolution test (paddle method) in the second fluid was carried out on the preparations obtained in Reference Examples 1 to 3, according to the Pharmacopoeia of Japan, 11th Edition. In each test, such an amount of beads as to contain 50 mg of PPA therein was used. The results are shown in FIG. 3. These preparations released out almost all of the active ingredient in about 5 hours in a first-order release. Needless to say, they do not have a sustained-release property.

What is claimed:

1. A process for manufacturing sustained-release two-layer preparations, wherein 1 part by weight of a water-soluble pharmaceutically active ingredient is suspended or melted in 1 to 10 parts by weight of a mixed melt consisting of two or more fats having different melting points, and while the temperature of the suspension or the melt is maintained at a level higher than the solidification point of the fat having a higher melting point, said suspension or melt is formulated into granules by means of spray-cooling, and then the granules obtained are annealed at a temperature which is lower than the melting point of the fat having a higher melting point but is higher than the melting point of the fat having a lower melting point.

2. The process as claimed in claim 1, wherein the mixture of fats comprises 1 part by weight of a fat having a higher melting point and 0.05 to 1 part by weight of a fat having a lower melting point.

3. A process according to claim 1 wherein there is a difference of at least 10° C. between the melting points of the two fats used.

* * * * *